United States Patent
Spijkerman et al.

(10) Patent No.: US 11,629,240 B2
(45) Date of Patent: Apr. 18, 2023

(54) FORMULATION OF DI(4-TERT-BUTYLCYCLOHEXYL) PEROXYDICARBONATE

(71) Applicant: NOURYON CHEMICALS INTERNATIONAL B.V., Arnhem (NL)

(72) Inventors: Geesje Klasina Spijkerman, Deventer (NL); Auke Gerardus Talma, Bathmen (NL); Markus Oliver Majoor, Amersfoort (NL); Antonie Den Braber, Arnhem (NL); Martin Hermanus Maria Jansen, Wijhe (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 136 days.

(21) Appl. No.: 16/955,537

(22) PCT Filed: Dec. 14, 2018

(86) PCT No.: PCT/EP2018/084893
§ 371 (c)(1),
(2) Date: Jun. 18, 2020

(87) PCT Pub. No.: WO2019/121371
PCT Pub. Date: Jun. 27, 2019

(65) Prior Publication Data
US 2021/0009786 A1   Jan. 14, 2021

(30) Foreign Application Priority Data

Dec. 19, 2017 (EP) .................... 17208546

(51) Int. Cl.
*C08K 5/14* (2006.01)
*C08K 3/36* (2006.01)
*C08K 5/103* (2006.01)
*C08K 5/105* (2006.01)

(52) U.S. Cl.
CPC .............. *C08K 5/14* (2013.01); *C08K 3/36* (2013.01); *C08K 5/103* (2013.01); *C08K 5/105* (2013.01); *C08K 2201/005* (2013.01)

(58) Field of Classification Search
CPC ............ C08K 5/14; C08K 5/103; C08K 5/105
See application file for complete search history.

(56) References Cited

U.S. PATENT DOCUMENTS

| 3,538,011 A | 11/1970 | van der Klaauw | |
| 4,801,667 A * | 1/1989 | Brand | C08F 18/24 526/213 |
| 10,689,337 B2 * | 6/2020 | Spijkerman | C08K 3/36 |
| 2019/0248983 A1 * | 8/2019 | Nagl | C07C 407/006 |

FOREIGN PATENT DOCUMENTS

| DE | 1618726 A1 | 4/1972 | |
| DE | 102011102682 A1 | 11/2012 | |
| EP | 0939103 A2 * | 9/1999 | |
| KR | 20020063181 A * | 8/2002 | |
| WO | WO-9749759 A1 * | 12/1997 | ............ C08F 8/50 |
| WO | 2012159726 A1 | 11/2012 | |
| WO | 2017089375 A1 | 6/2017 | |

OTHER PUBLICATIONS

Machine translation, retrieved December 20022 (Year: 2022).*
EPO, Extended European Search Report issued in Application No. 17208546.6, dated Apr. 20, 2018.
ISA-EPO, International Search Report issued in International Application No. PCT/EP2018/084893, dated Feb. 18, 2019.

* cited by examiner

*Primary Examiner* — Nicole M. Buie-Hatcher
(74) *Attorney, Agent, or Firm* — Lorenz & Kopf, LLP

(57) ABSTRACT

Powder formulation comprising 20-75 wt % of di(4-tert-butylcyclohexyl) peroxydicarbonate and 25-80 wt % of a phlegmatizer selected from the group consisting of ethylene glycol dibenzoate, phenyl benzoate, trimethylol propane tribenzoate, dimethylsulfon, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, and combinations thereof.

20 Claims, No Drawings

FORMULATION OF DI(4-TERT-BUTYLCYCLOHEXYL) PEROXYDICARBONATE

CROSS-REFERENCE TO RELATED APPLICATION

This application is a U.S. National-Stage entry under 35 U.S.C. § 371 based on International Application No. PCT/EP2018/084893, filed Dec. 14, 2018, which was published under PCT Article 21(2) and which claims priority to European Application No. 17208546.6, filed Dec. 19, 2017, which are all hereby incorporated in their entirety by reference.

TECHNICAL FIELD

The present invention relates to a formulation of di(4-tert-butylcyclohexyl) peroxydicarbonate.

BACKGROUND

Di(4-tert-butylcyclohexyl) peroxydicarbonate is an organic peroxide that is used as initiator in various reactions, including the curing of thermoset resins—e.g. unsaturated polyester resins, vinyl ester resins, and methacrylic resins—and the polymerization of various monomers.

Thermoset resins, in particular unsaturated polyester and vinyl ester resins, are cured by reacting them with ethylenically unsaturated monomer, which reaction is initiated by an organic peroxide. The conventional ethylenically unsaturated monomer is styrene.

Di(4-tert-butylcyclohexyl) peroxydicarbonate is presently available as a powder in neat, undiluted form, and as pastes. The pastes generally contain about 40 wt % di(4-tert-butylcyclohexyl) peroxydicarbonate and further about 60 wt % of solvents (e.g. glycols) and dispersants and/or fillers.

Solutions of di(4-tert-butylcyclohexyl) peroxydicarbonate in an inert, phlegmatizing solvent have turned out to be unstable.

Neat di(4-tert-butylcyclohexyl) peroxydicarbonate is subject to re-classification in terms of fire class rating: from Class II to Class I (US storage classification NFPA 400). The lower the class, the higher the risks and the lower the amount of peroxide that is allowed to be stored on site.

Di(4-tert-butylcyclohexyl) peroxydicarbonate pastes have a Class III rating. However, pastes have the disadvantage of being difficult to pump into the resin composition. Pastes require specific, expensive pumps and emptying drums containing the pastes is rather problematic.

A solution to that problem would be dissolution of the paste in the ethylenically unsaturated monomer, prior to pumping it to the reaction mixture. Unfortunately, however, the presently used solvents in such pastes (glycols) are not compatible with styrene.

Hence, there is a desire to provide a di(4-tert-butylcyclohexyl) peroxydicarbonate formulation that dissolves in styrene and is rated Class II (US storage classification NFPA 400), which means that its burning rate is between 60 and 300 kg/min At the same time, the formulation should not segregate during storage.

WO 2017/089375 discloses di(4-tert-butylcyclohexyl) peroxydicarbonate formulations with reduced burning rate. As phlegmatizers, this document discloses, amongst others, glycerol tribenzoate and dilauroyl peroxide.

Dilauroyl peroxide, however, is hard to dissolve in a curable resin. Dissolution requires either the use of a co-solvent or heating. The latter has a safety risk. Furthermore, as shown in the experimental section below, the effect of glycerol tribenzoate on the burning rate is limited and can be further improved. In addition, other objects, desirable features and characteristics will become apparent from the subsequent summary and detailed description, and the appended claims, taken in conjunction with the accompanying drawings and this background.

SUMMARY

It has now been found that stable formulations with a further reduced burning rate can be obtained by blending neat di(4-tert-butylcyclohexyl) peroxydicarbonate powder with certain phlegmatizers.

The present invention therefore relates to a powder formulation comprising:
20-75 wt % of di(4-tert-butylcyclohexyl) peroxydicarbonate and
25-80 wt % of a phlegmatizer selected from the group consisting of ethylene glycol dibenzoate, phenyl benzoate, trimethylol propane tribenzoate, dimethylsulfon, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, and combinations thereof.

It is noted that U.S. Pat. No. 3,538,011 and WO 2012/159726 disclose the phlegmatization of dibenzoylperoxide, bis(2,4-dichlorobenzoyl)peroxide and cyclohexanone peroxide with some of these phlegmatizers. However, their effect on the burning rate of peroxides, let alone di(4-tert-butylcyclohexyl) peroxydicarbonate, is neither disclosed nor suggested.

The formulation according to the present invention is preferably prepared by blending neat di(4-tert-butylcyclohexyl) peroxydicarbonate powder with the phlegmatizer. In a preferred embodiment, part of the phlegmatizer is added to a mixing device, after which the peroxide is added to the mixing device. The remaining part of the phlegmatizer is added to the mixing device after the peroxide has been added.

Before blending, the phlegmatizer can be milled, preferably such that 90 vol % of the particles has a size (d90) less than 500 microns, more preferably less than 400 microns, more preferably less than 300 microns, and most preferably between 150-250 microns. Smaller particles entail health and explosion risks due to dust formation. Larger particles are difficult to dissolve in a resin.

The neat di(4-tert-butylcyclohexyl) peroxydicarbonate powder preferably contains particles with a size (d90) less than 100 microns, and most preferably 10-40 microns.

Despite the significant difference in particle size between the peroxide and the phlegmatizer, it is—surprisingly—possible to obtain stable, non-segregating formulations of these two components.

DESCRIPTION

The following detailed description is merely exemplary in nature and is not intended to limit the invention or the application and uses of the invention. Furthermore, there is no intention to be bound by any theory presented in the preceding background of the invention or the following detailed description.

In contrast to conventional techniques for making peroxide formulations (such as in-situ preparation of the peroxide in the phlegmatizer or mixing of the phlegmatizer with an aqueous suspension of the peroxide), the above method allows for higher peroxide concentrations in the formulation. Furthermore, no drying steps are required since water is absent.

The formulation according to the present invention comprises 20-75 wt %, preferably 50-75 wt %, and most preferably 60-70 wt % di(4-tert-butylcyclohexyl) peroxydicarbonate; calculated as neat peroxide.

The formulation according to the present invention comprises 25-80 wt % preferably 25-50 wt %, and most preferably 30-40 wt % of a phlegmatizer.

The phlegmatizer is selected from the group consisting of ethylene glycol dibenzoate, phenyl benzoate, trimethylol propane tribenzoate, dimethylsulfon, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, and combinations thereof.

These phlegmatizers are solid at room temperature (20° C.), have a melting point above 50° C., and are soluble in unsaturated polyester resins.

Ethylene glycol dibenzoate (EGDB) and phenylbenzoate are the most preferred phlegmatizers.

The formulation according to the present invention preferably also comprises one or more anti-caking agents, in a preferred amount of 0.1-5 wt %, preferably 0.5-2 wt %, most preferably 0.8-1.2 wt %, based on phlegmatizer. Conventional anti-caking agents can be used. A preferred anti-caking is silica.

The powder formulation according to the present invention is preferably free of substantial amounts of other components.

The formulation of the present invention can be used in polymer modification processes, cross-linking reactions, (mass) polymerization processes, and curing processes of, for example, unsaturated polyester resins, vinyl ester resins, and acrylate resins, including ortho-resins, iso-resins, iso-npg resins, and dicyclopentadiene (DCPD) resins. Examples of such resins are maleic, fumaric, allylic, vinylic, and epoxy-type materials.

Curing processes using the formulation according to present invention are preferably performed at temperatures in the range 60-140° C. Examples of suitable curing techniques are SMC, BMC, pultrusion, filament winding, cured-in-place pipe (CIPP), and the manufacturing artificial stone.

EXAMPLES

Reference Example 1

Ethylene glycol dibenzoate (EGDB) flakes were milled to a d90 particle size of about 225 microns.

Different amounts of silica (MFIL-P(S), ex-Madhu Silica) were added after said milling.

The influence of silica on caking of EGDB was studied with caking tests, which were performed as follows.

Cylinders with a diameter of 40 mm diameter were filled with 30 gram EGDB. On top of the material, a weight was placed of either 240, 300, or 500 grams. The cylinders were stored in an oven for 48 hours, at either 30° C. or 40° C.

After cooling down, EGDB was removed from the cylinders and caking was judged visually. The results are displayed in Table 1, in which:

"severe caking" means: the cake remained a cake after removal of the cylinder and was hard to break up;

"caking" means: the cake remained a cake after removal of the cylinder but was easy to break up;

"slight caking" means: the cake broke during removal of the cylinder, but small, easy to break up lumps remained;

"no caking" means: the cake broke during removal of the cylinder and no lumps remained.

TABLE 1

| T (° C.) | Weight (g) | Silica (wt %) | | | | |
|---|---|---|---|---|---|---|
| | | 0 | 0.25 | 0.5% | 0.75 | 1 |
| 30° C. | 240 | ND[1] | ND | ND | No caking | No caking |
| 30° C. | 300 | | | | No caking | No caking |
| 30° C. | 500 | | | | Slight caking | No caking |
| 40° C. | 240 | Severe caking | Caking | Caking | No caking | No caking |
| 40° C. | 300 | Severe caking | Caking | Caking | No caking | No caking |
| 40° C. | 500 | Severe caking | Caking | Caking | Slight caking | No caking |

[1]ND = not determined

Example 2

Five formulations were prepared, each comprising di(4-tert-butylcyclohexyl) peroxydicarbonate and either (i) EGDB or (ii) EGDB containing 1 wt % silica as prepared in Example 1:

Formulation A comprising 60 wt % di(4-tert-butylcyclohexyl) peroxydicarbonate in EGDB.

Formulation B1 comprising 70 wt % di(4-tert-butylcyclohexyl) peroxydicarbonate in EGDB.

Formulation B2 comprising 70 wt % di(4-tert-butylcyclohexyl) peroxydicarbonate in EGDB comprising 1 wt % silica as prepared in Example 1.

Formulation C1 comprising 80 wt % di(4-tert-butylcyclohexyl) peroxydicarbonate in EGDB.

Formulation C2 comprising 80 wt % di(4-tert-butylcyclohexyl) peroxydicarbonate in EGDB comprising 1 wt % silica as prepared in Example 1.

Formulation D comprising 70 wt % di(4-tert-butylcyclohexyl) peroxydicarbonate in glycerol tribenzoate.

Formulation E comprising 70 wt % di(4-tert-butylcyclohexyl) peroxydicarbonate in phenyl benzoate.

These formulations where prepared by first de-agglomerating EGDB, GTB, and phenyl benzoate flakes in a Retsch hammer mill (type SK-1, rotational speed: 2800 rpm, Sieve: 1.5 mm), followed by mixing di(4-tert-butylcyclohexyl) peroxydicarbonate (Perkadox® 16, ex-AkzoNobel) with the de-agglomerated powder in a Kitchenaid Heavy Duty mixer, type KSSS, for 5 minutes.

Formulations B1 and B2 were subjected to a segregation test.

A sample was charged into a 15° tilted cylinder (stainless steel, 50 cm length, 10 cm diameter) and slowly rotated (7-8 rpm) around it's longitudinal axis. After 20 minutes, rotation was stopped and samples were taken from the upper, middle and lower part of the cylinder.

The peroxide content of all samples was determined by iodometric titration, by dissolving the sample in THF, adding KI, and titrating with sodium thiosulphate. The results (see Table 2) show that the samples differed in less than 5%, meaning that the tendency for segregation is negligible.

TABLE 2

|  | Formulation B1 | Formulation B2 |
| --- | --- | --- |
| Overall formulation | 69.8 | 70.2 |
| Upper layer | 69.6 | 70.0 |
| Middle layer | ND | 70.1 |
| Lower layer | 70.7 | 69.5 |

[1] ND = not determined

Example 3

In order to study the solubility of the formulations in different resins and in styrene, 0.5 grams of the formulations were added to a 100 ml beaker containing 50 gram resin or styrene and stirred with an overhead pitched blade stirrer (40 mm) at 4 rpm. Dissolution speed was judged visually. The results are compared with that of neat di(4-tert-butylcyclohexyl) peroxydicarbonate.

The following resins were used:
Palatal® P4 (a styrene-containing unsaturated polyester resin ex-DSM)
Duracon® 205 (an acrylate resin ex-Polyplastics)

Table 3 shows that the formulations all dissolve as quickly as or even quicker than neat di(4-tert-butylcyclohexyl) peroxydicarbonate.

TABLE 3

|  | Dissolution speed in: | | |
| --- | --- | --- | --- |
|  | Palatal® P4 | Duracon® | styrene |
| neat | 10.5 min | 3.5 min | <10 sec |
| Formulation C1 | 10.5 min |  |  |
| Formulation B1 | 8.0 min | 3.0 min |  |
| Formulation A | 6.0 min |  | <10 sec |

Example 4

Neat di(4-tert-butylcyclohexyl) peroxydicarbonate and formulations A, B1, C1, D, and E were subjected to burning tests. In these tests, 20×2 cm strips of the formulations were made on a flat stainless steel plate.

The strips were ignited by a yellow gas flame. The time required to burn the entire 20 cm strip was measured and listed in Table 4.

TABLE 4

| formulation | Time (sec) |
| --- | --- |
| A | 55 |
| B1 | 18 |

TABLE 4-continued

| formulation | Time (sec) |
| --- | --- |
| C1 | 11 |
| D | 6 |
| E | — (ignites but extinguishes in a few sec. |
| neat | 5 |

Example 5

Formulations B2 and C2 were subjected to external fire tests by the German Bundesanstalt für Materialforschung und -prüfung (BAM) in order to determine the burning rate and the corresponding storage.

Of each formulation, 17 packages (4G cardboard boxes with an inner plastic bag) were provided, each package containing 11.34 kg formulation.

One package was placed on one wooden pallet and surrounded with wood wool. The wooden pallet and the wood wool were ignited using a mixture of liquid fuels and an igniter. The irradiance was measured using infrared sensors arranged in pairs. The irradiance is a measure for the burning time, which can be used to calculate the burning rate.

The same experiment was repeated with six packages on one pallet and with ten packages on one pallet.

The burning rate of formulation B2 was 237 kg/min, which means that it is classified as US (NFPA 400) Class II (burning rate between 60 and 300 kg/min).

The burning rate of formulation C2 was 1018 kg/min, which means that it is classified as US (NFPA 400) Class I (burning rate between above 300 kg/min).

Example 6

To 100 g unsaturated polyesters resin (Palatal® P4), 100 g of quartz filler (Quarz Mehl M6) was added. After stirring, a peroxide (formulation) was added in an amount corresponding to 0.5 g neat peroxide.

The resulting mixture was poured into a test tube containing a thermocouple. The test tube was heated in a water bath of 82° C. The temperature of the mixture was recorded in time.

The Geltime (GT) is the time required for the mixture temperature to increase from 63.3° C. to 85.6° C.

The time to peak (TTP) is the time required to reach the maximum temperature.

The peak exotherm (PE) is the maximum temperature reached.

The minimum cure time (MCT) is the time lapsed starting from 63.3° C. until the maximum temperature.

TABLE 5

| Palatal P4 (g) | 100 | 100 | 100 | 100 | 100 | 100 | 100 |
| --- | --- | --- | --- | --- | --- | --- | --- |
| Quarz (g) | 100 | 100 | 100 |  |  |  |  |
| Perkadox® 16 (g) | 0.500 |  |  | 0.500 |  |  |  |
| Formulation A (g) |  | 0.794 |  |  | 0.794 |  |  |
| Formulation B1 (g) |  |  | 0.681 |  |  | 0.681 |  |
| Formulation B2 (g) |  |  |  |  |  |  | 0.681 |
| GT (min) | 2.0 | 2.1 | 2.1 | 2.2 | 1.9 | 1.9 | 2.0 |
| MCT (min) | 3.7 | 4.0 | 3.9 | 4.4 | 4.1 | 4.2 | 4.1 |
| TTP (min) | 5.6 | 6.2 | 6.2 | 8.2 | 7.6 | 7.7 | 8.2 |
| PE (° C.) | 117.6 | 115.9 | 120.3 | 165.4 | 161.3 | 159.2 | 163.2 |

These results show that EGDB does not negatively influence the cure of polyester resins.

Example 7

Example 6 was repeated except that the temperature of the water bath was 70° C.

The results are displayed in Table 6, and again show that EGDB does not negatively influence the cure of polyester resin.

TABLE 6

| | | | | |
|---|---|---|---|---|
| Palatal P4 (g) | 100 | 100 | 100 | 100 |
| Quarz (g) | | | | |
| Perkadox ® 16 (g) | 0.500 | | | |
| Formulation A (g) | | 0.794 | | |
| Formulation B1 (g) | | | 0.681 | |
| Formulation B2 (g) | | | | 0.681 |
| GT (min) | 5.5 | 4.7 | 5.3 | 5.7 |
| MCT (min) | 8.8 | 8.0 | 8.4 | 8.8 |
| TTP (min) | 13.3 | 11.5 | 12.2 | 13.2 |
| PE (° C.) | 147.5 | 144.8 | 146.5 | 146.7 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A powder formulation comprising:
   20-75 wt % of di(4-tert-butylcyclohexyl) peroxydicarbonate, and
   25-80 wt % of a phlegmatizer,
   wherein the phlegmatizer comprises one or more of ethylene glycol dibenzoate, phenyl benzoate, trimethylol propane tribenzoate, dimethylsulfon, ethylene glycol ditoluate, 1,3-propanediol ditoluate, ethylene glycol 4-tert-butylbenzoate, ethylene glycol monobenzoate monotoluate, 2,3-butanediol dibenzoate, and 4-methylphenyl benzoate acid ester,
   wherein the di(4-tert-butylcyclohexyl) peroxydicarbonate has a particle size $d_{90}$ of less than 100 microns, and the phlegmatizer has a particle size $d_{90}$ less 500 microns.

2. The powder formulation according to claim 1 comprising:
   50-75 wt % of the di(4-tert-butylcyclohexyl) peroxydicarbonate; and
   25-50 wt % of the phlegmatizer.

3. The powder formulation according to claim 2, wherein the phlegmatizer comprises ethylene glycol dibenzoate and/or phenyl benzoate.

4. The powder formulation according to claim 3, wherein $d_{90}$ of the di(4-tert-butylcyclohexyl) peroxydicarbonate is 1-40 microns and $d_{90}$ of the phlegmatizer is 150-250 microns.

5. The powder formulation according to claim 1 comprising:
   60-70 wt % of the di(4-tert-butylcyclohexyl) peroxydicarbonate; and
   30-40 wt % of the phlegmatizer.

6. The powder formulation according to claim 5, wherein the phlegmatizer comprises ethylene glycol dibenzoate.

7. The powder formulation according to claim 1, further comprising 0.1-5.0 wt % of an anti-caking agent.

8. The powder formulation according to claim 7, wherein the anti-caking agent comprises silica.

9. The powder formulation according to claim 7, substantially free of other components.

10. The powder formulation according to claim 1, comprising essentially no water.

11. The powder formulation according to claim 1, consisting of the di(4-tert-butylcyclohexyl) peroxydicarbonate, the phlegmatizer, and an anti-caking agent.

12. The powder formulation according to claim 1, wherein $d_{90}$ of the di(4-tert-butylcyclohexyl) peroxydicarbonate is 1-40 microns and $d_{90}$ of the phlegmatizer is 150-250 microns.

13. A process for the production of a powder formulation according to claim 1, comprising the step of physically mixing neat di(4-tert-butylcyclohexyl) peroxydicarbonate powder with the phlegmatizer.

14. The process according to claim 13, comprising adding a part of the phlegmatizer to a mixing device, thereafter adding the di(4-tert-butylcyclohexyl) peroxydicarbonate to the mixing device, and then adding the remaining part of the phlegmatizer to the mixing device.

15. A process for curing an unsaturated resin, comprising the step of adding the powder formulation of claim 1 to the resin and heating the resulting mixture at a temperature of 60-140° C.

16. The process according to claim 15, wherein the phlegmatizer comprises phenyl benzoate.

17. The process according to claim 15, wherein the resin comprises a polyester resin.

18. The process according to claim 15, wherein the resin comprises a vinyl ester resin or an acrylate resin.

19. The powder formulation according to claim 1, wherein the phlegmatizer comprises ethylene glycol dibenzoate and/or phenyl benzoate.

20. The powder formulation according to claim 19, wherein $d_{90}$ of the di(4-tert-butylcyclohexyl) peroxydicarbonate is 1-40 microns and $d_{90}$ of the phlegmatizer is 150-250 microns.

* * * * *